United States Patent
Danenberg

(10) Patent No.: US 9,901,724 B2
(45) Date of Patent: Feb. 27, 2018

(54) SKIN PUNCTURING APPARATUS FOR USE IN A NON-SURGICAL METHOD FOR ERADICATION OF TATTOOS

(75) Inventor: Noam Danenberg, Hod Hasharon (IL)

(73) Assignee: Hawk Medical Technologies Ltd., Tel Aviv (IL)

(*) Notice: Subject to any disclaimer, the term of this patent is extended or adjusted under 35 U.S.C. 154(b) by 565 days.

(21) Appl. No.: 14/111,282

(22) PCT Filed: Mar. 29, 2012

(86) PCT No.: PCT/IL2012/000135
§ 371 (c)(1),
(2), (4) Date: Dec. 9, 2013

(87) PCT Pub. No.: WO2012/140643
PCT Pub. Date: Oct. 18, 2012

(65) Prior Publication Data
US 2014/0094837 A1     Apr. 3, 2014

(30) Foreign Application Priority Data
Apr. 11, 2011   (IL) .......................................... 212262

(51) Int. Cl.
*A61M 37/00* (2006.01)
*A61B 17/34* (2006.01)
(Continued)

(52) U.S. Cl.
CPC ......... *A61M 37/0084* (2013.01); *A61B 17/34* (2013.01); *A61K 8/368* (2013.01);
(Continued)

(58) Field of Classification Search
CPC ....... A61B 17/205; A61B 17/20; A61B 17/34; A61B 17/3476; A61B 17/3478;
(Continued)

(56) References Cited

U.S. PATENT DOCUMENTS

| | | | | | |
|---|---|---|---|---|---|
| 4,180,068 | A | * | 12/1979 | Jacobsen | A61B 17/34 604/164.01 |
| 5,820,373 | A | * | 10/1998 | Okano | A61C 17/02 433/216 |

(Continued)

FOREIGN PATENT DOCUMENTS

| | | |
|---|---|---|
| WO | 2005/020828 A1 | 3/2005 |
| WO | 2007/015232 A1 | 2/2007 |

OTHER PUBLICATIONS

International Search Report/Written Opinion, dated Aug. 30, 2012, in corresponding International Application No. PCT/IL2012/000135.

(Continued)

*Primary Examiner* — Katrina Stransky
*Assistant Examiner* — Katherine Schwiker
(74) *Attorney, Agent, or Firm* — Francis J. Coffey; Dann, Dorfman, Herrell and Skillman, P.C.

(57) ABSTRACT

The invention is a skin puncturing apparatus for use in a non-surgical method for eradication of a tattoo from an area of skin. The apparatus comprises: (a) a handle section comprising a motor and gear assembly for causing a reciprocating motion to a shaft connected to the gear assembly; (b) a barrel section surrounding the shaft, the first end of the barrel section attached to the handle and the second end of the barrel section having a tip adapted to be placed in contact with the area of skin; (c) a bundle of needles attached by means of a needles holder to the distal end of the shaft; and (d) an inlet body comprising an inlet port through which cleaning solution is introduced into the tip located at the lower edge of the barrel section.

9 Claims, 7 Drawing Sheets

(51) Int. Cl.
*A61Q 1/14* (2006.01)
*A61K 8/368* (2006.01)

(52) U.S. Cl.
CPC ......... *A61M 37/0076* (2013.01); *A61Q 1/145* (2013.01); *A61K 2800/87* (2013.01); *A61K 2800/91* (2013.01)

(58) Field of Classification Search
CPC ........... A61B 2017/00769; A61B 2017/00747; A61B 2017/00756; A61B 2017/00761; A61B 2217/002; A61B 2217/005; A61B 2217/007; A61B 17/545; A61B 17/54; A61M 37/00; A61M 37/0015; A61M 37/0076; A61M 37/0084; A61M 2037/0007; A61M 2037/0023; A61M 2037/003; A61M 2037/0038; A61M 2037/0061; A61M 2037/0046; A61K 2800/91; A61Q 1/145; A61Q 1/14; A45D 2200/1063
See application file for complete search history.

(56) References Cited

U.S. PATENT DOCUMENTS

| | | |
|---|---|---|
| 7,905,854 B2 | 3/2011 | Hazut et al. |
| 2004/0186421 A1* | 9/2004 | Freeman ............ A61B 10/0035 604/39 |
| 2004/0186501 A1 | 9/2004 | Su |
| 2006/0142708 A1 | 6/2006 | Hazut et al. |
| 2007/0156095 A1* | 7/2007 | Hazut .................. A61B 17/205 604/173 |
| 2008/0208235 A1 | 8/2008 | Ulmer et al. |
| 2008/0221548 A1 | 9/2008 | Danenberg et al. |
| 2008/0319453 A1* | 12/2008 | Tavger ................ A61B 17/545 606/131 |

OTHER PUBLICATIONS

Extended European Search Report, dated Dec. 15, 2014, issued in connection with corresponding European Patent Application No. 12771038.2.

* cited by examiner

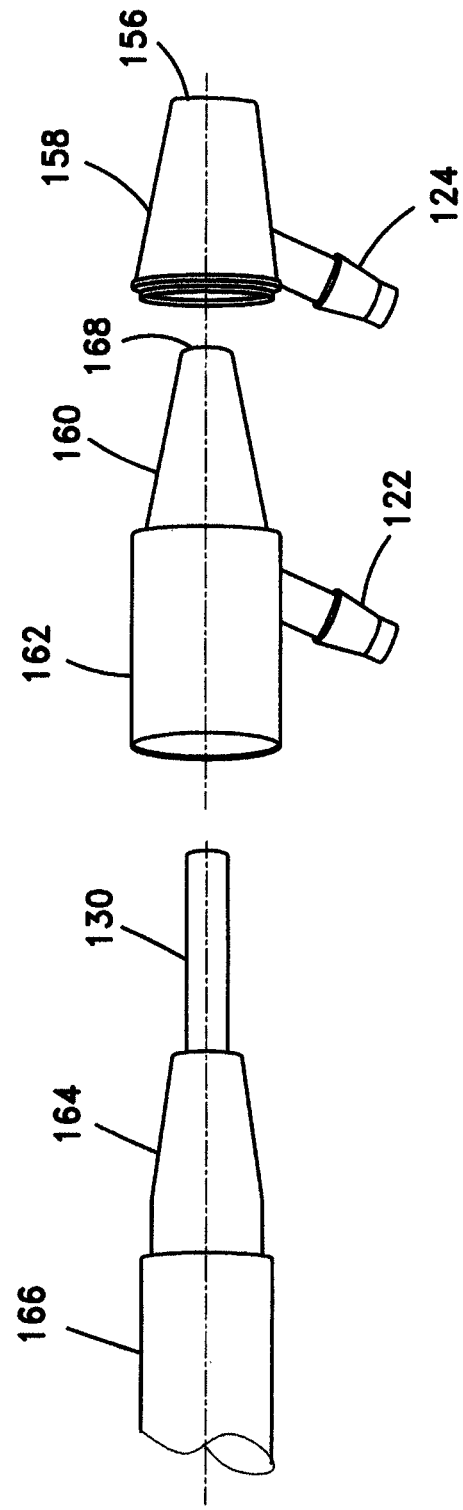

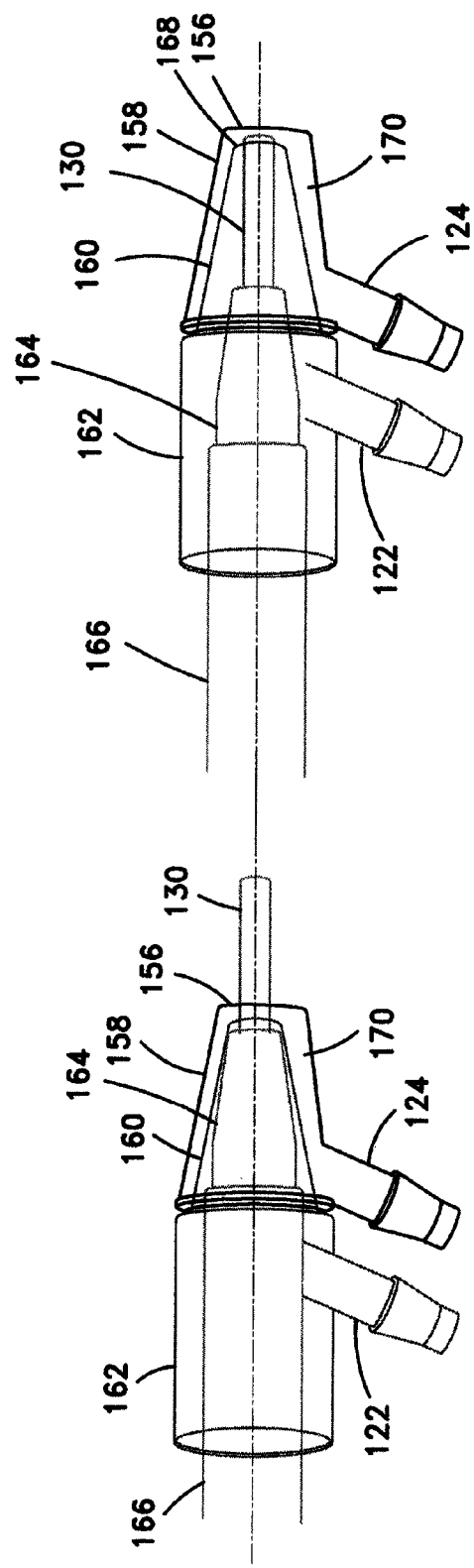

SKIN PUNCTURING APPARATUS FOR USE IN A NON-SURGICAL METHOD FOR ERADICATION OF TATTOOS

CROSS-REFERENCE TO RELATED APPLICATIONS

This application is the U.S. National Stage of International Application No. PCT/IL2012/000135, filed Mar. 29, 2012, which claims priority from Israeli Patent Application No. 212262, filed Apr. 11, 2011. The entire disclosure of each of the aforesaid applications is incorporated by reference in the present application.

FIELD OF THE INVENTION

The present invention relates to the field of cosmetic treatments. Specifically the present invention relates to the non-surgical eradication of tattoos from an area of skin.

BACKGROUND OF THE INVENTION

For cosmetic or a variety of other reasons, people often wish to have a tattoo removed from their skin. Topical ointments are often used to try to cover the tattoo. However, because the pigment is an integral part of the cells in the dermis, removing the pigmentation is not an easy task and can only be effectively accomplished by destroying and replacing the cells containing the pigments. Known methods of eradicating tattoos include:
  Dermabrasion, wherein skin is "sanded" (i.e., abraded) to remove the layers of skin containing the pigmentation;
  Cryosurgery, wherein the pigmented area is frozen prior to its removal; and
  Excision, wherein a dermatologic surgeon removes the pigmented skin with a scalpel and closes the wound with stitches. In some cases involving large areas of skin, a skin graft from another part of the body may be necessary.

These methods are typically quite painful and frequently leave white spots and occasionally scars.

Lasers offer a more precise and generally less damaging alternative to the abovementioned methods. Each procedure is done as a single treatment, or in a series of treatments. Patients may or may not require topical or local anesthesia. Lasers remove the pigment by producing short pulses of intense light, which pass through the top layers of the skin and are then selectively absorbed by the pigment. The laser energy causes the pigment to be fragmented into smaller particles, which are then removed by the body's immune system. One of the problems with laser treatment, especially for the removal of tattoos, is that the absorption of the laser energy is color dependent and that a given laser can only be used to remove pigments in a particular color range. Moreover, there are side effects of laser procedures including occasional burning, scaring, hyper pigmentation (an abundance of color in the skin at the treatment site) and hypo pigmentation (the treated area lacks normal skin color).

A less traumatic method for removing pigmented areas of skin are described in International Patent Applications WO2004/107995, WO2005/020828, and WO2007/015232 by the Applicant of the present application.

The method described in these publications is based on the known fact that the tattoo pigments are mainly enclosed within cells located in the dermis layer of the skin. Therefore, as a first step, the tattooed area of skin is repeatedly punctured by an array of needles attached to a skin puncturing device similar to a tattooing machine in order to mechanically destroy the cells and release the pigments. After that the pigment fractions can rise to the surface through the pores created by the needles. The problem is that within a very short time period of several minutes the pores close, preventing all of the pigments from being removed. It is for this reason that in the second step of the method a pad containing a salt-based granulated paste is applied to the surface of the skin at the treated area for a limited period of time that is generally on the order of 20 minutes and does not exceed one hour. The salt-based granulated paste exerts a strong hygroscopic force to suck the intercellular fluid and debris including particles of pigment and fragments of the destroyed cells to the surface thereby taking advantage of the limited time frame available before the pores close to maximize the amount of the tattoo pigment that is removed from the dermis.

The first patent application describes the basic method and apparatus. The second application describes an apparatus for carrying out the method. This apparatus comprises a mediating member attached to a device similar to a conventional tattoo machine and a mediating member that is attached to the skin puncturing device. The mediating member is in contact with the skin and provides means for drawing off the cellular fluids and debris that rises to the skin surface at the site of the punctured skin and means for washing the needles and surface of the skin with a suitable liquid if desired. The third application describes a modification to the apparatus. In particular this application describes modifications to the skin puncturing device that allow an aqueous solution to flow onto the needles and the treated area of skin on each down stroke of the needles and to be sucked away on each upstroke of the needles. In this way the needles and the area of skin are continually rinsed with fresh solution to remove cellular fluid and debris including tattoo ink pigments that rise to the surface during the puncturing phase of the method and to insure that the needles are clean when they penetrate the skin.

It is a purpose of the present invention to provide new embodiments of the apparatus that, when used to carry out the basic method developed by the applicant, provides more complete eradication of tattoos than has been previously attainable.

Further purposes and advantages of this invention will appear as the description proceeds.

SUMMARY OF THE INVENTION

In a first aspect the invention is a skin puncturing apparatus for use in a non-surgical method for eradication of a tattoo from an area of skin. The apparatus comprises:
  (a) a handle section comprising a motor and gear assembly for causing a reciprocating motion to a shaft connected to the gear assembly;
  (b) a barrel section surrounding the shaft, the first end of the barrel section attached to the handle and the second end of the barrel section having a tip adapted to be placed in contact with the area of skin;
  (c) a bundle of needles attached by means of a needles holder to the distal end of the shaft;
  (d) an inlet body comprising an inlet port through which cleaning solution is introduced into the tip located at the lower edge of the barrel section; and
  (e) an outlet body comprising an outlet port to which suction means are connected located proximally of the inlet body.

The apparatus of the characterized in that activating the motor causes, the bundle of needles to alternately be pushed out of the tip to puncture the area of skin and to be pulled back into the tip; and the inlet body is adapted such that, when a supply of fluid is attached to the inlet port, the fluid can flow continuously onto the needles in the bundle of needles.

The needles holder, the outlet body, and the outlet port in embodiments of the apparatus of the invention are adapted in one of the following ways:
  (a) such that the interior end of the outlet port is blocked when the bundle of needles is pushed out of the tip and unblocked when the bundle of needles is pulled back into the tip; or
  (b) such that the interior end of the outlet port is never blocked.

In a second aspect the invention is a method of using the skin puncturing apparatus of the first aspect in a non-surgical method for eradicating a tattoo from an area of skin. The method of the invention comprises:
  (a) connecting a supply of fluid to the inlet port;
  (b) connecting suction means to the outlet port;
  (c) causing fluid to flow from the supply of fluid through the inlet port;
  (d) activating the suction means; and
  (e) activating the motor of the apparatus for a predetermined period of time.

In embodiments of the method of the invention suction means are either not connected to the outlet port or, if suction means are connected to the outlet port, then the suction means are not activated.

In embodiments of the method the fluid comprises a chemical selected from the group comprising: EDTA, DMSO, Collagenase, Hyaluronidase, Papain, Bromelain hypertonic Saline, Salicylic Acid, Aloe, Bidentis, Kalanchoes, Eucalyptus, Chamomile, Calendula, *Salvia officinalis, Helichrysum arenarium*, and Hydrogen Peroxide. In one embodiment of the method the fluid is an aqueous solution of salicylic acid. In an embodiment of the invention the concentration of the salicylic acid in the aqueous solution is between 2% and 5%.

All the above and other characteristics and advantages of the invention will be further understood through the following illustrative and non-limitative description of preferred embodiments thereof, with reference to the appended drawings.

BRIEF DESCRIPTION OF THE DRAWINGS

FIGS. 5A, 5B, and 5C symbolically show the main features of the principal components of the distal end of the barrel section of the apparatus of the invention;
and
FIGS. 6A, 6B, and 6C schematically show how the washing of the needles and the suction take place in this embodiment of the invention.

DETAILED DESCRIPTION OF PREFERRED EMBODIMENTS

Figure 1:
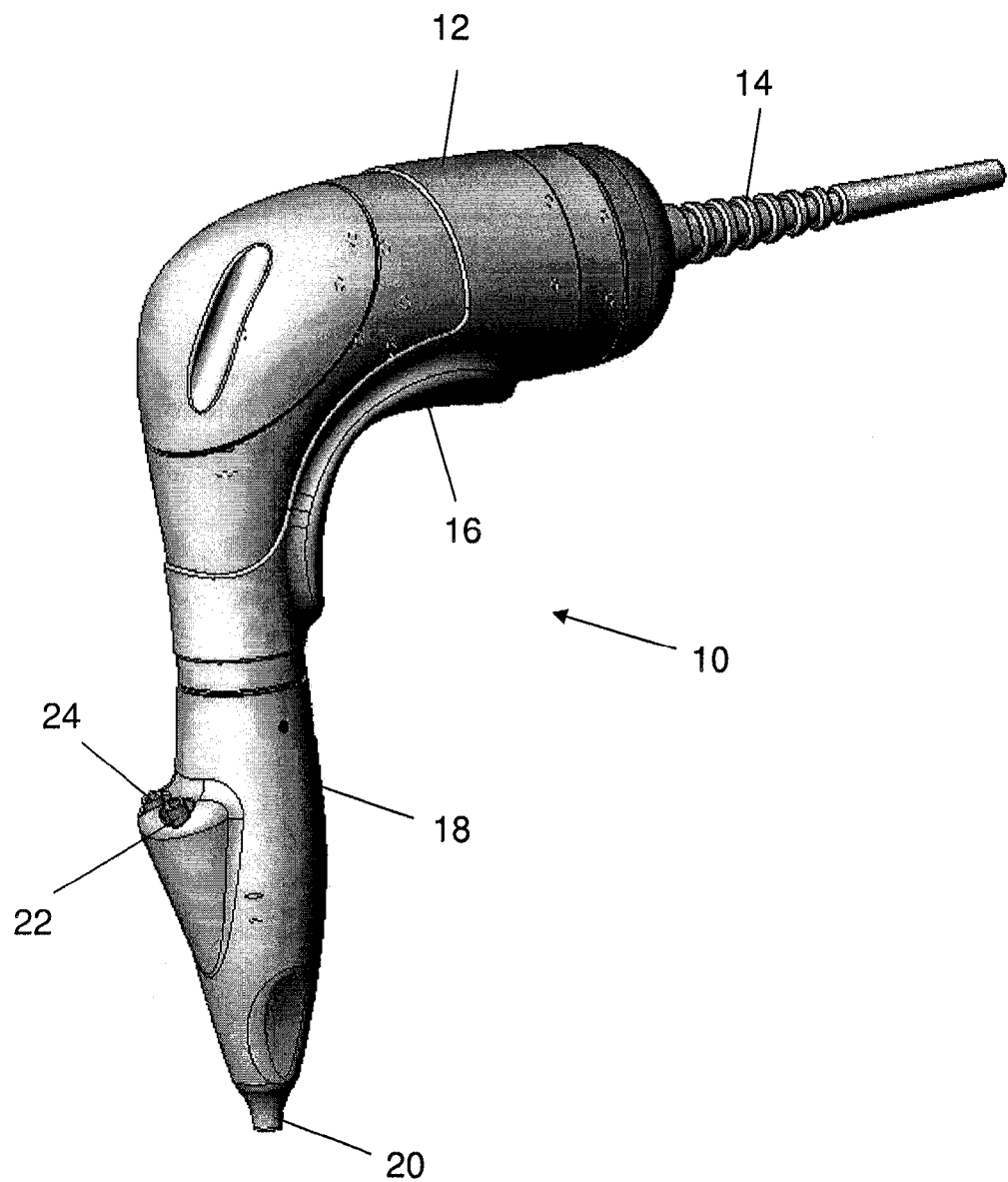
FIG. 1 shows a prior art skin puncturing device.

FIG. 1 shows an external view of the skin puncturing apparatus described previously in WO2007/015232. As said hereinabove, the skin puncturing apparatus is very similar in many ways to a conventional tattooing machine. For easy handling, the apparatus 10 is shaped like a pistol comprising handle section 12, barrel section 18, and a trigger 16 to activate the apparatus.

Inside handle 12 is a motor that is connected to a shaft inside of barrel section 18 of the device through a gear assembly. When rotated by the motor, the gears impart a reciprocating motion to the shaft; thereby causing the shaft to move back and forth inside the barrel. The power source can be batteries, either external or internal or an external source of electricity, e.g. a transformer that delivers a current of 0 to 1 amperes at 6 to 12 volts, through power cord 14.

Also seen in FIG. 1 are the tip 20 of the barrel, outlet port 22, and inlet port 24. Tip 20 is shaped so that when it is pressed against the skin a hermetic seal is created isolating the interior of the barrel from the outside. Ports 22 and 24 are connected respectively to a source of suction and a fluid supply container (neither of which are shown in the figures or described in detail herein).

Figure 2A:
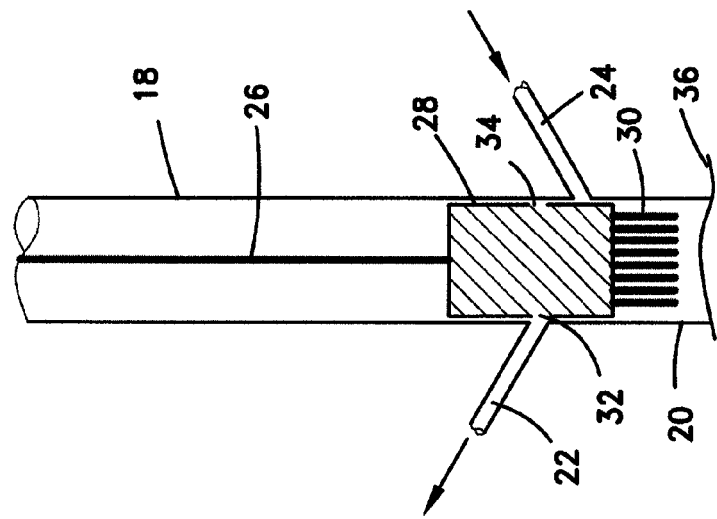
FIG. 2A and FIG. 2B are schematic cross-sectional views of the barrel portion of the prior art device shown in FIG. 1.
Figure 2B:
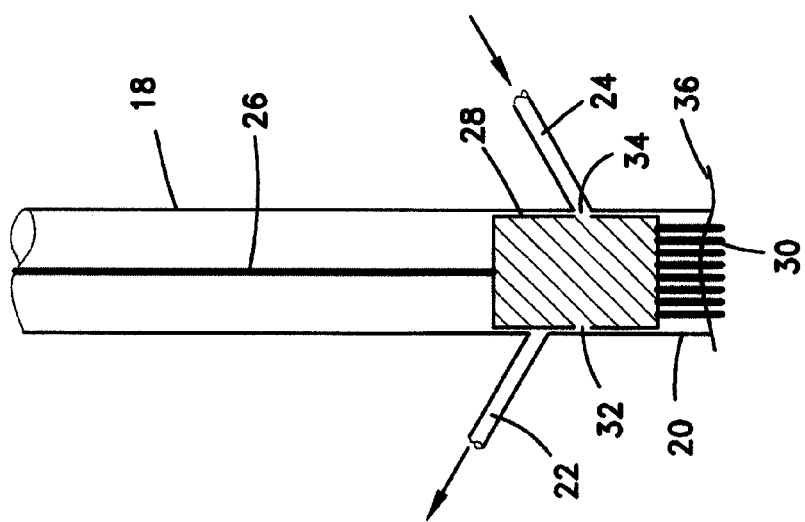

FIG. 2A and FIG. 2B are schematic cross-sectional views showing the interior of barrel portion 18 of apparatus 10. These figures have been greatly simplified and the locations of some of the parts rearranged in order to more easily describe the operation of the apparatus. Fixedly attached to shaft 26 are cylindrical valve 28 and array of needles 30. As the shaft 26 is moved up and down by the motor, the array of needles 30 is alternately pushed through the outer layer of skin 36 into the dermis and withdrawn from the skin into the tip 20 of barrel 18.

The number of needles in the array depends on, amongst other factors, the size of the apparatus. A typical array can comprise, for example, between 7 to 38 needles. The apparatus is designed such that when the piston 26 is at it lowest position, the needles extend through tip 20 and penetrate the skin to a depth of between 0 to 3 mm, the exact depth depending on the location of the area to be treated and determined such that the tips of the needles do not pass through the dermis into the underlying fatty layer.

Cylindrical valve 28 is essentially a cylindrically shaped piston that provides a hydraulic seal that separates the volume inside the barrel 18 above valve 28 from the volume below it. Valve 28 has two openings, inlet hole 34 and outlet hole 32, in its side wall. Both of these openings are fluidly connected to the bottom of valve 28, such that fluid in the fluid supply container can alternately flow through inlet port 24 and inlet hole 34 in order to wash the needles and skin surface and be sucked out of the tip 20 of the barrel 18 through outlet hole 32 and outlet port 22. The function of the cylindrical valve is to insure that for a part of each stroke the area of skin being treated is rinsed with clean fluid and that for the remainder of the stroke the fluid and pigments that have collected in the tip 20 during the first part of the stroke are sucked out of it.

The timing of the washing and suction is important in order to continually rinse the needles with fresh solution to remove cellular fluid and pigment and insure that only clean needles penetrate the skin. The timing is illustrated in FIGS. 2A and 2B. On the down stroke (FIG. 2A) inlet hole 34 is lined up with inlet port 24 allowing fluid from the fluid supply container to flow onto needles 30 and the surface of the skin. At the same time outlet hole 32 and outlet port 22 are not aligned so that the source of suction is not connected to the interior of tip 20. On the upstroke (FIG. 2B) as the needles are pulled out of the skin, the alignment of the holes and ports is reversed and the fluid is prevented from entering tip 20 while the suction draws the fluids and pigment out of the tip of the device. By operating in this manner it is seen that, on the one hand, there is an absolute separation between the clean and the "dirty" fluid and, on the other hand, an essentially instantaneous change between the state in which fluid flows into the tip and the state in which it is sucked out of the tip. The "dirty" fluid is sucked from the tip as the needles are withdrawn from the skin in order to minimize the amount of solution that permeates through the holes made by the needles and reaches the cells damaged by the needles inside the dermis. It is important to rinse the needles during each cycle to prevent the transport of pigments and cell material that adhered to the needles during a first cycle back down into the dermis on the next cycle.

Extensive tests carried out with devices constructed as shown in FIGS. 1, 2A, and 2B, have revealed improved results in removing pigments when compared to carrying out the method without rinsing the needles. However it has been observed that in practice the needles are not 100% cleaned on each down stroke as expected. The reasons for this are several including: the fact that the pigments and cellular debris adhere to the needles more strongly than anticipated; the angle at which the cleaning fluid is introduced to the apparatus allows it only to flow downward over the surface of the needle and adhered material; the cleaning solution is not in contact with the surface of the needles for sufficient time to remove enough of the adhered material; and the configuration of the device does not allow the pressure and/or flow rate of the incoming fluid to be increased enough to significantly influence the results of the cleaning in a single down stroke.

Figure 3:
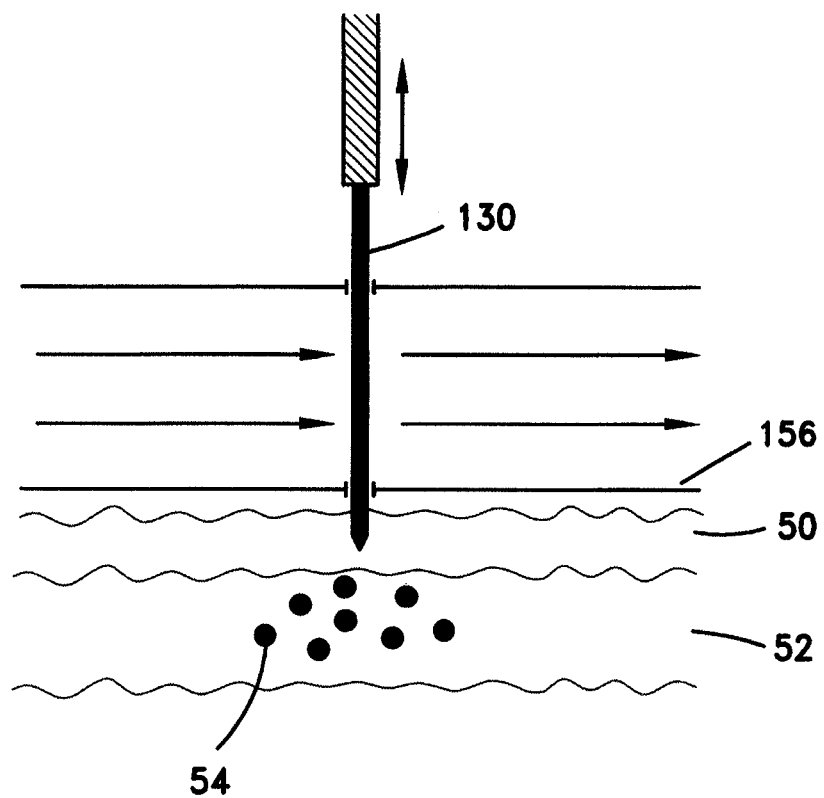
FIG. 3 schematically shows the direction impact of the aqueous cleaning solution with the needles.

The present invention is a skin puncturing apparatus designed to overcome the above problems with the prior art device as possible. The general idea behind the invention is to redirect at least part of the flow of the solution that is used to clean the needles in the manner shown schematically in FIG. 3. In FIG. 3 the distal edge 156 of the tip of the apparatus is shown resting on the area of the skin at the location of the tattoo 54 that is to be eradicated. Needle 130 is cyclically moved in the direction shown by the double headed arrow as described herein above down through the epidermis 50 and into the dermis layer 52 of the skin and back up into the tip of the apparatus. A fluid is introduced into the tip of the apparatus and channeled such that at least a portion of it flows close to the lower edge of the apparatus in the direction shown by the single headed arrows. In this way the fluid does not "flow" down the needle as in the prior art but strikes the needle at right angles maximizing the force of the impact to "knock" the debris off of the needles. In addition the design of the apparatus allows the pressure of the stream of solution to be increased and also the solution to flow continuously and not just on the down stroke as in the prior art, thereby increasing the time that the needle is being cleaned.

The fluid used to clean the needles can theoretically be either a gas or a liquid however in practice it is easier to use a liquid. Several different types of liquid have been tried including distilled water, EDTA, DMSO, Collagenase, Hyaluronidase, Papain, Bromelain hypertonic Saline, Salicylic Acid, Aloe, Bidentis, Kalanchoes, Eucalyptus, Chamomile, Calendula, *Salvia officinalis, Helichrysum arenarium*, and Hydrogen Peroxide. Reasonable results have been achieved with all of these but the best results to date have been achieved by using an aqueous solution of salicylic acid at a concentration of between 2% and 5%.

Figure 4:
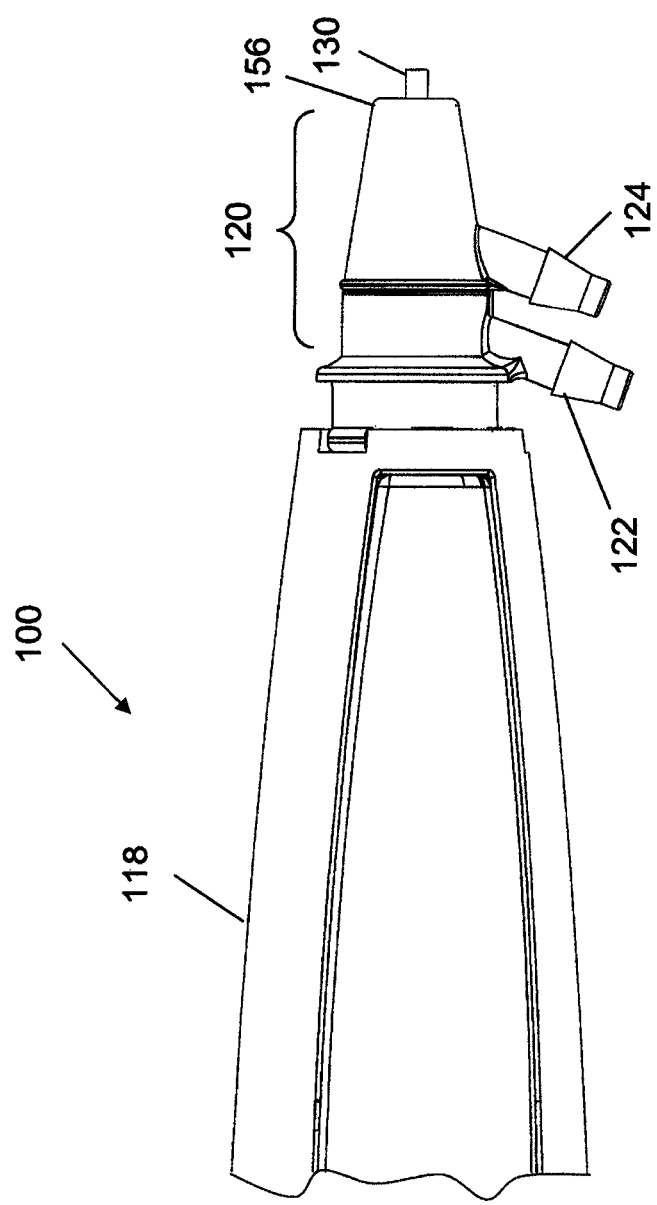
FIG. 4 schematically shows the distal end of the apparatus of the invention.

FIG. 4 schematically shows the distal end of the apparatus 100 of the invention. Seen in the figure are part of the barrel section 118, tip 120 of the barrel section, distal edge of the tip 156, a bundle of needles 130, an inlet port 124 through which the cleaning solution is introduced into tip 120 and an outlet port 122 to which suction means are connected and through which "dirty" solution can be drawn out of the tip. The remainder of the apparatus, e.g. handle, trigger, and motor to move the needles, are similar to those in the prior art apparatus described herein above with reference to the device of WO2007/015232.

FIGS. 5A, 5B, and 5C symbolically show the main features of the principal components of the distal end of barrel section 118. FIG. 5A shows inlet body 158 which comprises inlet port 124. Inlet body 158 has the shape of a hollow truncated cone whose small diameter end is the distal edge 156 of tip 120 of apparatus 100. FIG. 5B shows hollow cylindrically shaped outlet body 162, which comprises outlet port 122 on its side and hollow cone shaped extension 160 having distal edge 168. Extension 160 fits inside the interior of inlet body 158 and is dimensioned such that there is a space 170 (see FIGS. 6A to 6C) between the outer wall of extension 160 and the inner wall of inlet body 158. Inlet body 158 is hermetically attached to outlet body 162, which is in turn hermetically attached to barrel section 118 of the apparatus.

FIG. 5C shows the bundle of needles 130 held firmly at its proximal end by conically shaped extension 164 of needle holder 166. The bundle of needles is inserted into the interior of outlet body 162 and extension 160. The proximal end of the needles holder 166 is attached to a shaft that is moved longitudinally back and forth in a reciprocal manner when the motor in the apparatus is activated. The motion of the shaft causes the needles to move back and forth alternately being pushed out of the tip of the apparatus through the distal edge 156 and pulled back into the apparatus.

The number of needles in bundle 130 depends on, amongst other factors, the size of the tattoo to be removed and the strength of the motor employed. A bundle can comprise, for example, between seven to thirty eight needles with a standard bundle comprising twenty to thirty needles. In this invention the needles are solid and as smooth as possible in order to make it more difficult for debris to adhere to them and to make it easier to remove any debris that does adhere.

The apparatus is designed such that the needles can extend past the lower edge 156 of the tip and penetrate the skin to a depth of between 0 to 3 mm, the exact depth depending on the location of the area to be treated and determined such that the tips of the needles do not pass through the dermis into the underlying fatty layer.

Figure 6C:
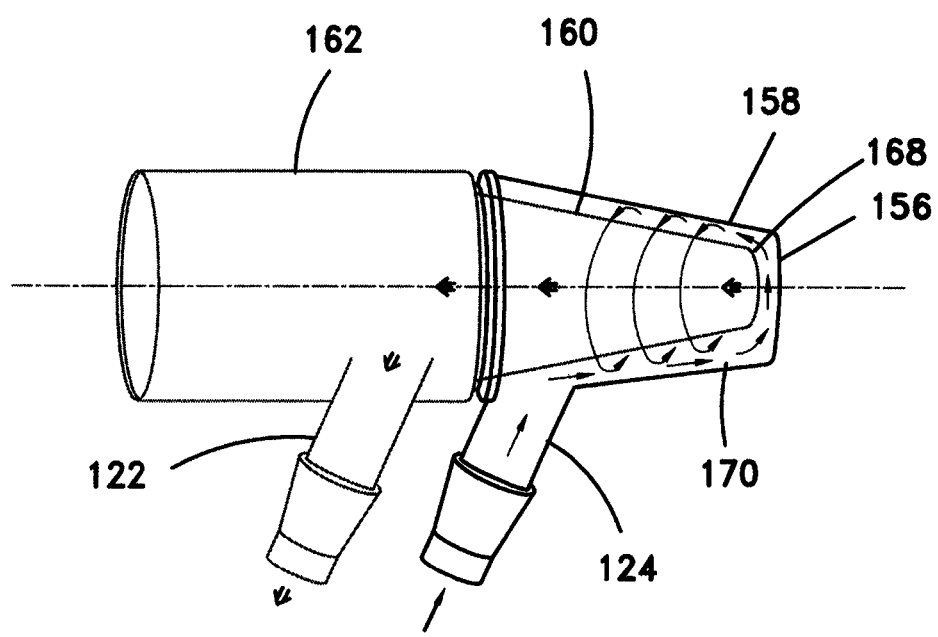

FIGS. 6A, 6B, and 6C schematically show how the washing of the needles and the suction take place in this embodiment of the invention. When bundle of needles 130 is pushed forward out of the tip of the apparatus as shown in FIG. 6A, the outer surface of needles holder 166 blocks the end of outlet port 122 preventing the suction means from drawing liquid out of the tip of the apparatus. When bundle of needles 130 is pulled back into the tip of the apparatus as shown in FIG. 6B, the end of outlet port 122 is unblocked allowing the suction means to draw liquid out of the tip of the apparatus. While the outlet port is alternately blocked and unblocked, the inlet port 124 is always opened allowing cleaning solution to be continuously streamed into the space 170 thereby continuously washing the needles.

FIG. 6C shows the same features as FIGS. 6A and 6B with the exception of needles holder 166, extension 164, and the bundle of needles 130. In FIG. 6C the single arrows schematically show how the cleaning fluid is forced into the apparatus through inlet port 124, fills the space 170 between the inlet body 158 and the extension 160 of outlet body 162 and streams in a direction essentially perpendicular to the needles as the pass back and forth through the space between distal edge 168 of extension 160 and distal edge 156 of inlet body 158 that is in contact with the skin surface. The double arrows schematically indicate the path of the cleaning fluid as it is drawn out of the apparatus through outlet port 122.

In another embodiment the outlet port 122 and/or the outlet body 162, and or the needles holder 166 is slightly modified such that when the bundle of needles 130 is exits the tip of the apparatus to penetrate the skin, as shown in FIG. 6A, the end of the outlet port 122 is not blocked. In this embodiment both clean solution is continuously streamed into the tip of the apparatus to wash the needles and suction is continuously applied to withdraw the dirty solution.

Both of the embodiments of the apparatus described herein above can be operated in another mode. Simply by not activating the suction means then there is provided continuous washing of the needles with no suction. This mode is less likely to be used than the ones that use suction, either continuous or periodic, because of the problem of collecting the dirty solution that will run off the skin of the person being treated. Nevertheless the apparatus can be operated in this mode and the method successfully carried out if circumstances dictate its use.

Although embodiments of the invention have been described by way of illustration, it will be understood that the invention may be carried out with many variations, modifications, and adaptations, without departing from its spirit or exceeding the scope of the claims.

The invention claimed is:

1. A skin puncturing apparatus for use in a non-surgical method for eradication of a tattoo from an area of skin, said apparatus comprising:
   (a) a handle section comprising a motor and gear assembly for causing a reciprocating motion to a shaft connected to said gear assembly;
   (b) a barrel section surrounding said shaft, said barrel section having a first end and second end, the first end of said barrel section attached to said handle and the second end of said barrel section having a tip;
   (c) a bundle of needles attached by a needles holder to a distal end of said shaft; characterized in that,
   A. said tip comprises:
      (i) an inlet body comprising an inlet port on a side of the inlet body, said inlet body having the shape of a hollow truncated cone whose small diameter end is a distal edge of said tip;
      (ii) a cylindrically shaped outlet body comprising an outlet port on a side of the outlet body and a hollow cone shaped extension having a distal edge that fits into an interior of said inlet body; and
      (iii) a space between an outer wall of said cone shaped extension of said outlet body and an inner wall of said inlet body;
   B. the reciprocating motion of said shaft moves said bundle of needles back and forth in an interior of said hollow cone shaped extension of the outlet body alternately pushing said bundle of needles out of said tip and pulling said bundle of needles back into said tip; and
   C. said inlet body and said outlet body are configured such that fluid flowing through said inlet port fills said space and is channeled to flow continuously through a space between the distal edge of the hollow cone shaped extension of the outlet body and the distal edge of the inlet body striking the needles at right angles and is drawn out of said apparatus through the interior of said hollow cone shaped extension of the outlet body in a direction parallel to said needles into said outlet body and through said outlet port.

2. The apparatus of claim 1, wherein said needles holder, said outlet body, and said outlet port are adapted in one of the following ways:
   (a) such that an interior end of said outlet port is blocked when said bundle of needles is pushed out of said tip and unblocked when said bundle of needles is pulled back into said tip; or
   (b) such that the interior end of said outlet port is never blocked.

3. A method of using the skin puncturing apparatus of claim 1 in a non-surgical method for eradicating a tattoo from an area of skin, said method comprising:
   (a) connecting a supply of fluid to the inlet port;
   (b) connecting a source of suction to said outlet port;
   (c) causing fluid to flow from said supply of fluid through said inlet port;
   (d) activating said source of suction; and
   (e) activating the motor of said apparatus for a predetermined period of time.

4. The method of claim 3, wherein the source of suction is not activated and the source of suction is either not connected or is connected to the outlet port.

5. The method of claim 3, wherein the fluid comprises a chemical selected from the group comprising: EDTA, DMSO, Collagenase, Hyaluronidase, Papain, Bromelain hypertonic Saline, Salicylic Acid, Aloe, Bidentis, Kalanchoes, Eucalyptus, Chamomile, Calendula, Salvia oficinalis, Helichrysum arenarium, and Hydrogen Peroxide.

6. The method of claim 3, wherein the fluid is an aqueous solution of salicylic acid.

7. The method of claim 6, wherein the concentration of the salicylic acid in the aqueous solution is between 2% and 5%.

8. A skin puncturing apparatus, said apparatus comprising:
   (a) a handle section comprising a motor and gear assembly for causing a reciprocating motion to a shaft connected to said gear assembly;
   (b) a barrel section surrounding said shaft, said barrel section having a first end and second end, the first end of said barrel section attached to said handle and the second end of said barrel section having a tip;
   (c) a bundle of needles attached by a needles holder to a distal end of said shaft;
   characterized in that,
   A. said tip comprises:
      (i) an inlet body comprising an inlet port, said inlet body having the shape of a hollow truncated cone whose small diameter end is a distal edge of said tip;
      (ii) a cylindrically shaped outlet body comprising an outlet port on a side of the outlet body and a hollow cone shaped extension having a distal edge that fits into an interior of said inlet body; and
      (iii) a space between an outer wall of said cone shaped extension of said outlet body and an inner wall of said inlet body;
   B. the reciprocating motion of said shaft moves said bundle of needles back and forth in an interior of said hollow cone shaped extension of the outlet body alternately pushing said bundle of needles out of said tip and pulling said bundle of needles back into said tip; and
   C. said inlet body and said outlet body are configured such that fluid flowing through said inlet port fills said space and is channeled to flow continuously through a space between the distal edge of the hollow cone shaped extension of the outlet body and the distal edge of the inlet body striking the needles at right angles and is drawn out of said apparatus through the interior of said hollow cone shaped extension of the outlet body in a direction parallel to said needles into said outlet body and through said outlet port.

9. The apparatus of claim 8, wherein said needles holder, said outlet body, and said outlet port are adapted in one of the following ways:
   (a) such that an interior end of said outlet port is blocked when said bundle of needles is pushed out of said tip and unblocked when said bundle of needles is pulled back into said tip; or
   (b) such that the interior end of said outlet port is never blocked.

\* \* \* \* \*